United States Patent [19]

Bryson, Sr.

[11] Patent Number: 5,388,762
[45] Date of Patent: Feb. 14, 1995

[54] DEVICE FOR DISPENSING A VAPORIZABLE MATERIAL

[75] Inventor: John D. Bryson, Sr., Milwaukee, Wis.

[73] Assignee: Vaportek, Inc., Sussex, Wis.

[21] Appl. No.: 44,224

[22] Filed: Apr. 7, 1993

[51] Int. Cl.$^6$ ............................................. A61L 9/04
[52] U.S. Cl. ...................... 239/56; 239/327; 222/3
[58] Field of Search .................. 239/34, 53–57, 239/60, 326, 327; 222/153, 3, 633

[56] References Cited

U.S. PATENT DOCUMENTS

| | | | |
|---|---|---|---|
| 2,620,095 | 12/1952 | Buchan | 222/633 |
| 2,708,595 | 5/1955 | Ludwig | 239/59 |
| 2,737,416 | 3/1956 | Behr et al. | 239/337 |
| 3,101,905 | 8/1963 | Hoenig | 239/59 |
| 3,785,556 | 1/1974 | Watkins | 239/6 |
| 4,096,994 | 6/1978 | Bryson | 239/57 |
| 4,306,679 | 12/1981 | Dusek et al. | 239/59 |
| 4,327,056 | 4/1982 | Gaiser | 239/56 |
| 4,372,490 | 2/1983 | Le Caire, Jr. et al. | 239/59 |
| 4,572,375 | 2/1986 | Baer | 239/56 |
| 4,610,394 | 9/1986 | Bryson | 239/57 |
| 4,858,831 | 8/1989 | Spector | 239/56 |
| 4,869,407 | 9/1989 | Booth, Jr. et al. | 239/326 |
| 5,148,984 | 9/1992 | Bryson, Jr. et al. | 239/58 |

FOREIGN PATENT DOCUMENTS

| | | | |
|---|---|---|---|
| 39070 | 8/1931 | France | 239/327 |

*Primary Examiner*—Karen B. Merritt
*Attorney, Agent, or Firm*—Michael, Best & Friedrich

[57] ABSTRACT

Disclosed herein is a dispenser comprising an inner member including a portion having an axis and a first end closed by a transverse wall, being resiliently displaceable in the direction of the axis between a collapsed condition and a normally extended condition, and defining an interior cavity adapted to contain a substance in the form of a vapor, an outer member movable relative to the inner member with respect to the axis and including a generally cylindrical portion in closely fitting telescopic relation to the inner member and having a first open end adjacent the transverse wall of the portion of the inner member, and a second end, and a wall closing the second end of the outer member cylindrical portion, and an aperture in at least one of the inner and outer members for affording air flow therethrough relative to the interior cavity in response to displacement of the inner member portion between the collapsed and extended conditions, whereby, the application of force in the direction of the axis causes relative axial movement in the direction affording displacement of the inner member portion to the collapsed condition with accompanying discharge of air with the substance in vapor form, and whereby release of the application of force causes axial movement of the outer member relative to the inner member in the direction affording re-extension of the inner member portion to the normally extended condition.

17 Claims, 4 Drawing Sheets

DEVICE FOR DISPENSING A VAPORIZABLE MATERIAL

BACKGROUND OF THE INVENTION

1. Technical Field

The invention relates generally to devices adapted for dispensing a vaporizable material or substance into the ambient air.

2. Relation to Prior Art

Devices adapted to dispense a vaporizable material into the ambient air are known.

Attention is directed to the following U.S. Patents:
Watkins U.S. Pat. No. 3,785,556 Jan. 15, 1974
Bryson U.S. Pat. No. 4,096,994 Jun. 27, 1978
Bryson U.S. Pat. No. 4,610,394 Sep. 9, 1986
Bryson U.S. Pat. No. 5,148,984 Sep. 22, 1992

SUMMARY OF THE INVENTION

The invention provides a dispenser comprising an inner member including a portion having an axis and a first end closed by a transverse wall, being resiliently displaceable in the direction of the axis between a collapsed condition and a normally extended condition, and defining an interior cavity adapted to contain a substance in the form of a vapor, an outer member movable relative to the inner member with respect to the axis and including a generally cylindrical portion in closely fitting telescopic relation to the inner member and having a first open end adjacent the transverse wall of the inner member portion, and a second end, and a wall closing the second end of the outer member cylindrical portion, and aperture means in at least one of the inner and outer members for affording air flow therethrough relative to the interior cavity in response to displacement of the inner member portion between the collapsed and extended conditions, whereby, the application of force in the direction of the axis causes axial movement of the outer member relative the inner member in the direction affording displacement of the inner member portion to the collapsed condition with accompanying discharge of air with the substance in vapor form from the interior cavity through the aperture means to the outer atmosphere, thereby dispensing the substance, and whereby release of the application of force causes axial movement of the outer member relative to the inner member in the direction affording re-extension of the inner member portion to the normally extended condition and inflow of air from the outer atmosphere into the interior cavity.

The invention also provides a dispenser comprising an inner member including a bellows portion having an axis and a first end closed by a transverse wall, being resiliently displaceable in the direction of the axis between a collapsed condition and a normally extended condition, and defining an interior cavity adapted to contain an envelope having a wall which is permeable to a substance contained therein and through which the substance passes into the immediately surrounding atmosphere as a vapor, an outer member movable relative to the inner member with respect to the axis, and including a generally cylindrical portion in closely fitting telescopic relation to the inner member and having a first open end adjacent the transverse wall of the bellows portion, and a second end, and a wall closing the second end of the outer member cylindrical portion, and means including an open area located in each of the inner and outer members and movable relative to each other in response to relative movement between the inner and outer members between a first position wherein the open areas are in registration to afford air flow therethrough relative to the interior cavity and a second position wherein the open areas are spaced from each other to prevent air flow relative to the interior cavity, whereby the application of force in the direction of the axis causes axial movement of the outer member relative the inner member in the direction affording displacement of the bellows portion to the collapsed condition with accompanying discharge of air with the substance in vapor form from the interior cavity through the open area to the outer atmosphere, thereby dispensing the substance, and whereby release of the application of force causes axial movement of the outer member relative to the inner member in the direction affording re-extension of the bellows portion to the normally extended condition and inflow of air from the outer atmosphere into the interior cavity.

The invention also provides a dispenser comprising an inner member including a cylindrical portion having an axis and opposite first and second ends, a first transverse wall closing the first end of the cylindrical portion, and a bellows portion extending from the second end of the cylindrical portion, having an open end remote from the cylindrical portion, being resiliently displaceable in the direction of the axis between a collapsed condition and a normally extended condition, and defining an interior cavity adapted to contain an envelope having a wall which is permeable to a substance contained therein and through which the substance passes into the immediately surrounding atmosphere as a vapor, an outer member movable relative to the inner member with respect to the axis and including a generally cylindrical portion in closely fitting telescopic relation to the cylindrical portion of the inner member and having a first open end extending beyond the bellows portion and to the cylindrical portion of the inner member, and a second end, and a transverse wall closing the second end of the cylindrical portion of the outer member, and an aperture located in each of the inner and outer members and movable relative to each other in response to relative movement between the inner and outer members between a first position wherein the apertures are in registration to afford air flow therethrough relative to the interior cavity and a second position wherein the apertures are spaced from each other to prevent air flow relative to the interior cavity, whereby, the application of force in the direction of the axis causes axial movement of the outer member relative the inner member in the direction affording displacement of the bellows portion to the collapsed condition with accompanying discharge of air with the substance in vapor form from the interior cavity through the apertures to the outer atmosphere, thereby dispensing the substance, and whereby release of the application of force causes axial movement of the outer member relative to the inner member in the direction affording re-extension of the bellows portion to the normally extended condition and inflow of air from the outer atmosphere into the interior cavity.

Other features and advantages of the invention will become apparent to those skilled in the art upon review of the following detailed description, claims, and drawings.

IN THE DRAWINGS

Figure 2:
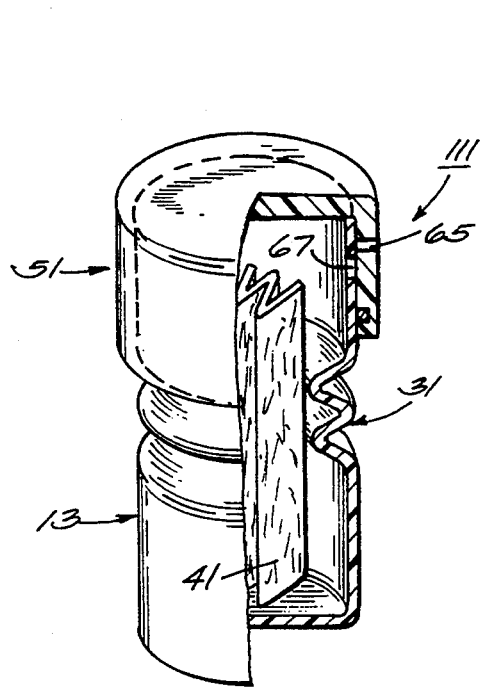
FIG. 2 is a perspective view, partially broken away and in section, of a second embodiment of a dispenser incorporating various of the features of the invention.

Before one embodiment of the invention is explained in detail, it is to be understood that the invention is not limited in its application to the details of the construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

GENERAL DESCRIPTION

Figure 1:
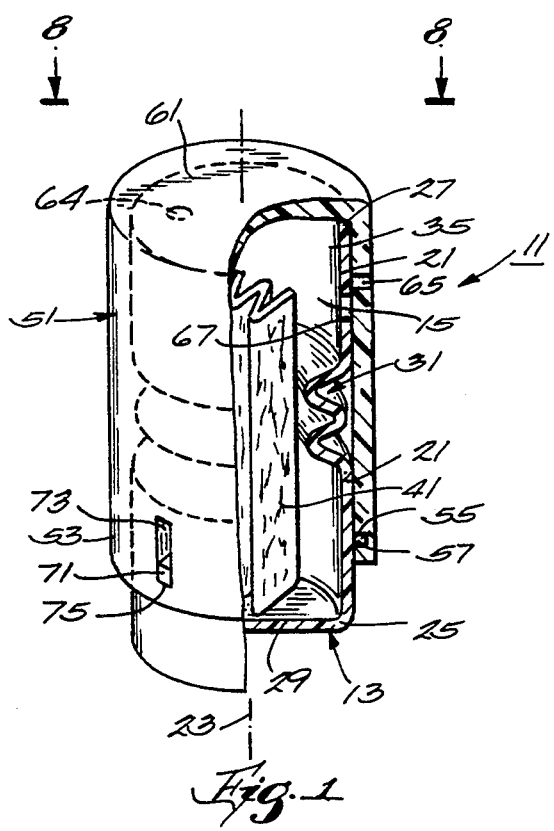
FIG. 1 is a perspective view, partially broken away and in section, of a first embodiment of a dispenser incorporating various of the features of the invention.

Shown in FIG. 1 is one preferred embodiment of a dispenser 11 which includes an inner member 13 defining an interior chamber or cavity 15 which is closed except for an open upper or top end 27 and including a resiliently collapsible portion. More specifically, the inner member 13 is preferably of one piece blow-molded construction and includes a cylindrical portion 21 having an axis 23 and a first or lower end 25 and second or upper end 27. The first or lower end 25 of the cylindrical portion 21 is closed by a transverse or end wall 29. The open upper or top end 27 facilitates entry into the interior chamber or cavity 15 and removal therefrom of a package or envelope 41 of a substance to be dispensed.

Extending intermediate the lower and top ends 25 and 27 of the cylindrical portion 21 is a bellows portion 31 which is resiliently collapsible, i.e., which is normally in an extended condition and which is resiliently displaceable to a collapsed condition in response to the application, in the axial direction, of a suitable force and which, upon the removal of the force, automatically and resiliently expands to its extended condition.

Preferably, the package or envelope 41 is of thin wall construction and contains a liquid substance to be dispensed and the envelope 41 is fabricated of a plastic material which is permeable to the substance. One example of such a package is disclosed in U.S. Pat. No. 3,785,556. Thus, when in a closed or steady state condition, the liquid substance in the envelope 41 will permeate through the thin wall of the envelope and emerge in vapor form. When the air in the interior cavity 15 is saturated with the substance (in vapor form), flow of the substance from within the envelope 41 will cease. Thus the air in the cavity 15 becomes saturated in response to a given amount of the substance flowing through the wall.

The dispenser 11 also includes a relatively rigid outer member or cover or sleeve 51 which is telescopically assembled with and movable in relation to the inner member 13 and which includes an open ended cylindrical portion 53 which movably telescopically engages the cylindrical portion 21 of the inner member 13 to guide relative movement therebetween and to, in effect, provide a seal between the inner and outer members 13 and 51.

If desired, one of the cylindrical portions 21 and 53 can be provided with an annular groove 55 to accept a sealing O-ring 57 which tightly sealingly engages both of the cylindrical portions 21 and 53 to prevent air flow between the telescopically engaged cylindrical portions 21 and 53. In another embodiment, a conventional lip seal can be employed between the inner and outer members 13 and 51 to prevent air flow therebetween.

The other end of the cylindrical portion 53 is closed by a transverse wall 61.

Means are provided for affording escape of vapor from the interior chamber or cavity 15 in response to axial collapse of the inner member consequent to axial movement of the sleeve 51 relative thereto. While other constructions can be employed, in the disclosed construction, such means comprises a relatively small aperture 65 in the side wall of the sleeve 51 and an opening 67 in the upper part of the cylindrical wall 21 of the inner member 13, which opening and aperature come into registration incident to downward movement of the sleeve 51 relative to the inner member 13.

In operation, there is little or no air flow through the aperature 65 when the dispenser 11 is in relaxed or extended condition, i.e. when the bellows portion 31 is extended and the opening 67 is out of register with the small aperture 65. Under such circumstances, the air in the inner cavity 15 of the dispenser 11 will, in time, become saturated with a given amount of the substance to be dispensed in vapor form.

However, upon the application of force in the direction of the axis 23 to effect collapse of the bellows portion 31, the outer member 51 will move relative to the inner member 13 in the direction toward the transverse end wall 29 of the inner member 13 so as to collapse the bellows portion 31 and, as the bellows portion 31 collapses, the aperture 65 and opening 67 will come into registration to afford dispensing the air saturated with the substance (in vapor forth) out of the cavity 15 through the aperture 65 and opening 67 and into the atmosphere. While other distances can be employed, in the construction disclosed in FIG. 1, the inner and outer members 11 and 51 are movable through a distance of one half inch of relative axial movement between the extended and collapsed projections.

When the application of force is discontinued, the resilient bellows portion 31 will again expand, thereby simultaneously drawing into the cavity 15 a new charge of fresh air which, over time, will again become saturated with the vapor form of the substance. In addition, full extension of the bellows portion serve to located the aperture 65 and opening 67 out of registration with each other. Thereafter, the dispenser 11 can then again be collapsed by application of sufficient force to collapse the bellows portion 31, thereby dispensing or discharging another substantially controlled quantity of the substance in vapor form.

Thus the preferred embodiment enables repeated discharge of a relatively constant amount of substance. Preferably, the substance is a suitable air freshener, although other substances can be employed.

Stop means can also be provided for releasably preventing disassembly of the outer member 51 from the inner member 13 consequent to attempted excessive (beyond normal) outward movement of the outer member 51 relative to the inner member 31. While various arrangements can be employed, in the disclosed construction, such means for releasably preventing disassembly of the inner and outer members 13 and 51 can be provided by a projection 71 provided on one of the inner and outer members 13 and 51 and a vertically extending slot 73 which is provided on the other of the inner and outer members 13 and 51 and which receives the projection 71. The axially extending slot includes an end wall or stop 75 which engages the end of the rib or projection 71 at the end of normal relative movement between the inner and outer members 13 and 51, thereby preventing excessive outward movement of the outer member 51 relative to the inner member 13. In addition, the axially extending groove 73 can be axially spaced from the annular sealing groove 55 to simultaneously provide sealing, and prevention of excessive axially outward movement of the outer member 51 relative to the inner member 13 while engagment of the projection 71 and the stop 75 normally prevents over travel, the projection 71 can be displaced inwardly to disengage the sleeve 51 and thereby to permit disassembly of the sleeve 51 from the inner member 13 to facilitate removal of an expended package and replacement thereof.

Figure 8:
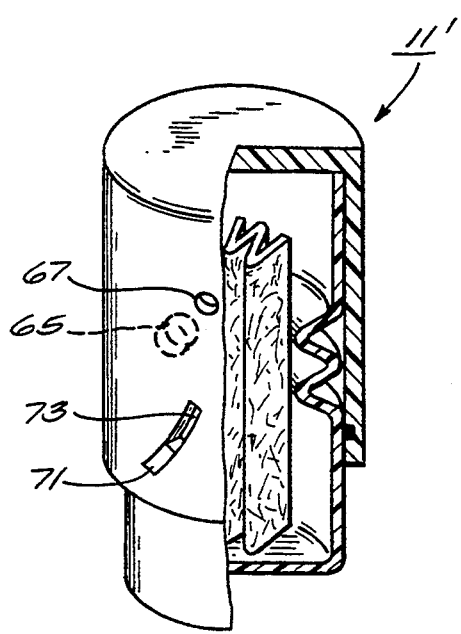
FIG. 8 is a perspective view, partially broken away and in section, of another embodiment of a dispenser incorporating various of the features of the invention.

While in the disclosed arrangements, the aperture 65 and opening 67 are axially displaced relative to their registered and non-registered positions in response to relative axial movement, there is shown in FIG. 8, another embodiment providing a dispenser 11', which is similar to the dispenser 11 and which includes an aperture 65 and opening 67 which are spaced angularly and vertically from each other when the dispenser 11' is in relaxed condition and moved into register in response to axial and rotational movement of the inner and outer members 13 and 15. In such a case the slot 23 would be helical.

Preferably, the one piece blow molded inner member 13 is fabricated of polypropelene plastic, while the outer sleeve or member 51 which is not routinely exposed to the substance being dispensed, can be fabricated of ABS plastic which provides a more pleasing outer appearance.

Figure 10:
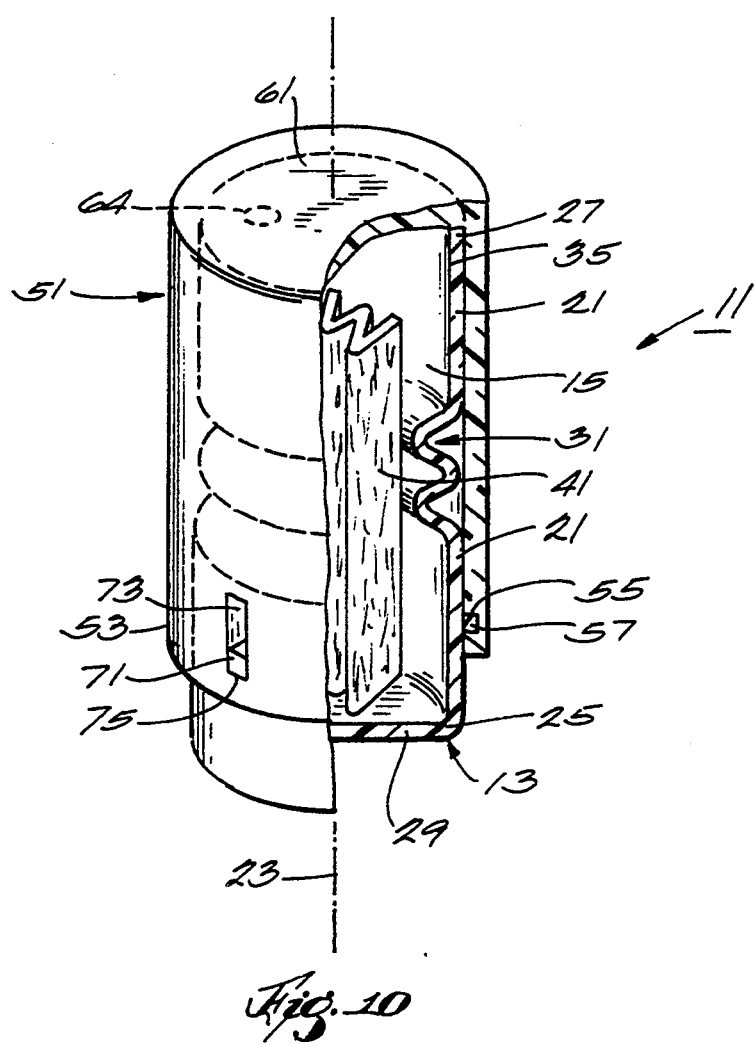
FIG. 10 is a perspective view, partially broken away and in section, of still another embodiment of a dispenser incorporating various of the features of the invention.

In still another embodiment, and as shown in FIG. 10, single restricted aperture 64 can be located in the end wall 61 of the outer sleeve or member 51, which aperture communicates directly with the interior space or cavity 15 within the inner member 13. While this arrangement provides continuing communication between the interior space or cavity 15 in the inner member 13 and the atmosphere surrounding the outer sleeve 51, in the absence of relative movement between the inner and outer members 13 and 51, there is very little air flow through the restricted opening.

Shown in FIG. 2 is another dispenser 111 which is similar to the dispenser 11 except that the outer member 51 is axially much smaller than in FIG. 1 and in that outer member 51, when assembled on the inner member 13, is releasably fixed against axial movement relative to the outer member 51. The cover or outer member 51 can be assembled by screw thread means or by any other suitable means, including but not limited to receipt of a projection, such as the projection 71, into a mating opening, such as a slot 73 which extends horizontally, i.e., perpendicular to the axis 23. In this embodiment, the bellows portion 31 of the inner member 13 is at least partially exposed when in extended condition. The bellows portion 31 can also be at the end of the inner member 13 remote from the outer member or cover 51.

One disadvantage of this arrangement is that there is considerably more exposure of the inner member 13 which has a less aesthetically desirable exterior surface than with respect to the embodiment shown in FIG. 1, wherein substantially the entire bellows portion 31 is covered by the outer member or cover 51.

Figure 3:
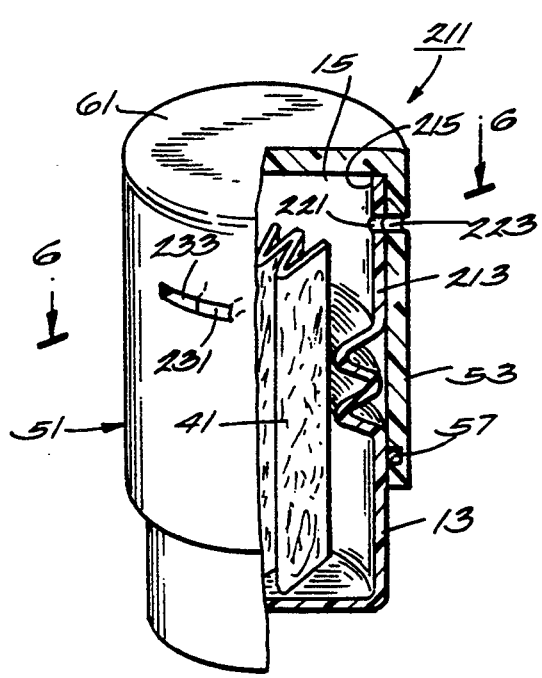
FIG. 3 is a perspective view, partially broken away and in section, of a third embodiment of a dispenser incorporating various of the features of the invention.
Figure 6:
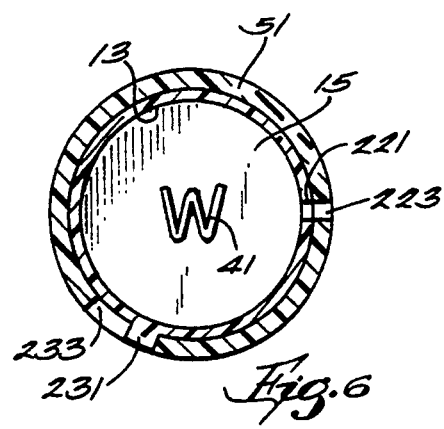
FIG. 6 is a sectional view taken along line 6—6 of FIG. 3 and showing the dispenser in the dispensing condition.
Figure 7:
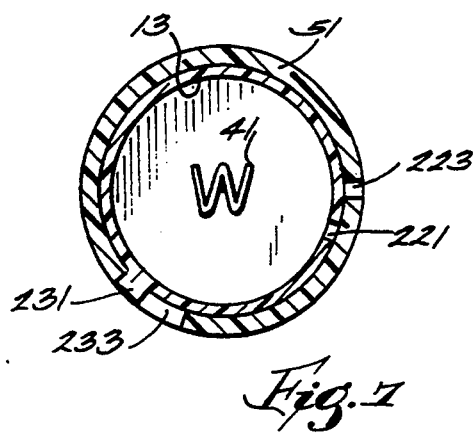
FIG. 7 is a view similar to FIG. 6 showing the dispenser in the non-dispensing condition.

Shown in FIG. 3 is another preferred dispenser 211 which is similar to the dispenser 11 shown in FIG. 1. As in the embodiment shown in FIG. 1, the inner member 13 includes a second cylindrical portion 213 which has an open end 215 engaging the transverse wall 61 of the outer member 51 and permitting removal of spent envelope 41 and replacement: with a fresh envelope 41 when the inner and outer members 13 and 51 are disassembled.

Discharge of the substance (in vapor form) from the envelope 41 in the cavity 15 in the inner member 13 is facilitated by registerable apertures 221 and 223. The aperture 221 is located in the second cylindrical portion 213 of the inner member 13 and the aperture 223 is located in the cylindrical portion 53 of the outer member 51. More specifically, as the inner and outer members 13 and 15 are rotatable relative to each other, the apertures 221 and 223 are movable relative to each other between open, registered positions and spaced positions out of registration with each other.

Means are also provided for releasably retaining the inner and outer members 13 and 51 in assembled relation and for permitting disassembly thereof, and for limiting rotary movement between the inner and outer members to afford movement of the apertures between the registered and non-registered positions. While other arrangements can be employed, in the disclosed construction, the inner member 13 includes a projection 231 which is received in a locking slot 233 which extends circumferentially to allow sufficient rotary relative movement of the inner and outer members 13 and 51 to enable full registration of the apertures 221 and 223, thus enabling discharge of the substance (in vapor form) and to fully separate or space the apertures, thus preventing air flow and consequent substance discharge. Thus, the projection and slot arrangement serves both to retain the inner and outer members 13 and 51 in assembled relation and to limit relative rotary movement therebetween. It is also noted that the projection and slot arrangement prevents axial movement between the second cylindrical portion 213 of the inner member 13 and the cylindrical portion 53 of the outer member 51. However, such limitation of relative axial movement does not prevent collapse of the bellows portion 31 and relative movement of the bellows portion 31 and lower or outer cylindrical portion 21 of the inner member 13 relative to the cylindrical portion 53 of the outer member 51. It is also noted that the inner blow molded member 13 is sufficiently resiliently flexible to permit sufficient deformation thereof to afford assembly and disassembly of the projection 231 into and out of the slot 233 so as to afford assembly and disassembly, and thereby to facilitate replacement of a new envelope 41 when the substance in the previous envelope 41 has been fully expended.

As before, a sealing O-ring 57 can be employed between the second cylindrical portion 213 of the inner member 13 and the cylindrical portion 53 of the outer member 51 if desired. However, if the cylindrical portions 213 and 53 are sufficiently closely fitted, such a sealing ring can be omitted.

Also, the apertures 221 and 223 can be arranged to move rotatively relative to each other in response to axial movement between the inner and outer members, as already discribed with respect to the embodiment shown in FIG. 8.

Figure 4:
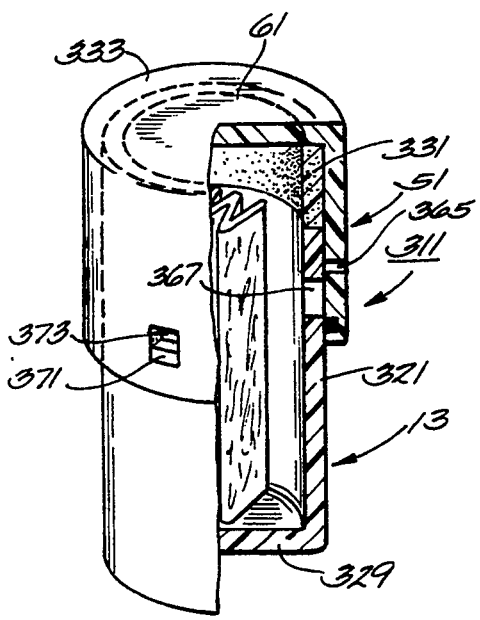
FIG. 4 is a perspective view, partially broken away and in section, of a fourth embodiment of a dispenser incorporating various of the features of the invention.

Shown in FIG. 4 is still another dispenser 311 which is similar to the dispensers 11 and 211 shown in FIGS. 1 and 3 except that the inner member 13 does not include a bellows portion but includes a cylindrical portion 321 which is closed at its outer end by a transverse wall 329 and which, at its other end, is open and is engaged with a resiliently collapsible cylindrical portion 331 fabricated of sponge-like material, which collapsible portion 331 is sandwiched between the cylindrical portion 321 and the transverse wall 61 of the outer member 51 and which includes an outer end 333 in engagement with the transverse wall 61 of the outer sleeve or member 51. In this embodiment, the cylindrical wall of the outer member 51 is provided with a restricted aperture 365 which, when the inner and outer members 13 and 51 are in their relatively extended position, is spaced from an axially extending opening 367 in the cylinder portion 321, which aperture 365 comes into registration with the opening 367 in response to downward axial movement of the outer member 51 relative to the inner member 13. When the inner and outer members 13 and 51 move axially relative to each other to and from the collapsed position, air flow sufficient to discharge the substance occurs during collapsing movement and the interior cavity 15 is recharged with fresh air during extending movement.

Suitable means such as a projection 371 and a locking slot 373 can be employed to selectively permit disassembly and reassembly of the inner and outer members 13 and 51 and, if desired, suitable groove and O-ring means can be provided for forming a seal between the cylindrical portions 321 and 53 of the inner and outer members 13 and 51.

Figure 5:
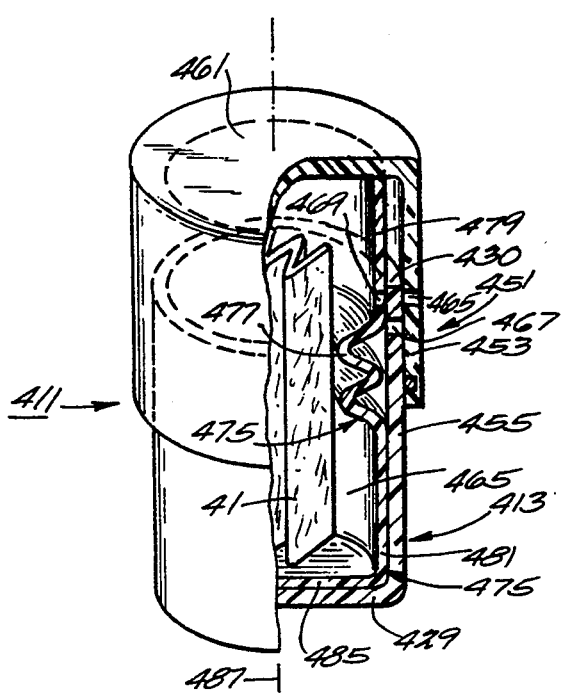
FIG. 5 is a perspective view, partially broken away and in section, of a fifth embodiment of a dispenser incorporating various of the features of the invention.

Shown in FIG. 5 is still another dispenser 411 wherein a relatively rigid inner cylindrical member 413 is closed at one end by a transverse wall 429 and open at the other end 430 and wherein a relatively rigid outer member or sleeve 451 includes a cylindrical portion 453 in telescopic and closely fitting relation to the cylindrical wall 455 of the inner member 413, and a transverse wall 461 closing the sleeve cylindrical portion 453 adjacent the open end 430 of the inner cylindrical member 413. Enclosed in a cavity 465, defined between the inner and outer members 413 and 451, is a bellows member 475 which, preferably, is of one-piece blow-molded construction, which includes a resiliently collapsible central bellows portion 477 communicating at the opposite ends thereof with respective cylindrical portions 479 and 481, which is closed at the outer end by a wall 485, and which is open at the other end.

In order to facilitate selective discharge of the substance, the outer member 451 includes a restricted aperture 465 and the inner member 413 includes an opening 467 which is spaced from the open end 430, and which is out of registry with the aperture 465 when the inner and outer members 413 and 451 are in their normal extended positions. In addition, the bellows member 475 includes an opening 469 in general alignment with the restricted aperture 465 in the outer member 456. The substance is discharged incident to collapsing telescopic movement of the inner and outer members 413 and 451, which movement causes collapse of the blow-molded bellows portion 477, and movement of the aperture 465 relative to the opening 467 from axially spaced non-registered positions preventing air flow into and out of the inner bellows member 477 to registered positions enabling substance discharge. Thus, when the inner and outer members 413 and 451 move from the extended position to the collapsed position, the opening 467 moves into a position in registration with the aperture 465 and the opening 469. When the inner and outer members 413 and 451 are in their fully extended position, the opening 467 is out of register with the aperture 465 and opening 460, thereby preventing air flow relative to the interior cavity 465 of the bellows member 475.

Figure 9:
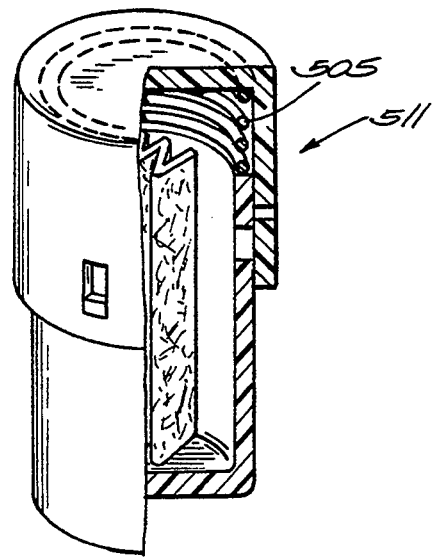
FIG. 9 is a perspective view, partially broken away and in section, of still another embodiment of a dispenser incorporating various of the features of the invention.

Shown in FIG. 9 is still another embodiment of a dispenser 511 which is similar to the dispenser 311 shown in FIG. 4, except that the collapsible portion 331 is replaced by a bellows spring 505. Spring arrangements other than the spring 505 can also be employed.

Various of the features of the invention are set forth in the following claims.

I claim:

1. A dispenser comprising an inner member which is of one piece constructed, which includes a first end closed by a transverse wall, a cylindrical portion having an axis and an end, and a bellows portion extending axially from said end of said cylindrical portion, which is resiliently displaceable in the direction of said axis between a collapsed condition and a normally extended condition, and which defines an interior cavity adapted to contain a substance in the form of a vapor, an outer member movable relative to said inner member with respect to said axis and including a generally cylindrical portion in closely fitting telescopic relation to said cylindrical portion of said inner member and having a first open end receiving said inner member, and a second end, and a wall closing said second end of said outer member cylindrical portion, and aperture means in at least one of said inner and outer members for affording air flow therethrough relative to said interior cavity in response to displacement of said inner member portion between said collapsed and extended conditions, whereby, the application of force in the direction of said axis causes axial movement of said outer member relative said inner member in the direction affording displacement of said inner member to the collapsed condition with accompanying discharge of air with the substance in vapor form from said interior cavity through said aperture means to the outer atmosphere, thereby dispensing the substance, and whereby release of the application of force causes axial movement of said outer member relative to said inner member in the direction affording re-extension of said inner member to the normally extended condition and inflow of air from the outer atmosphere into said interior cavity.

2. A dispenser in accordance with claim 1 wherein said inner and outer members include means for releasably permitting disassembly of said inner and outer members.

3. A dispenser in accordance with claim 1 wherein said inner and outer members include means for limiting axial movement between said inner and outer members.

4. A dispenser in accordance with claim 1 wherein said inner and outer members are movable rotatably relative to each other.

5. A dispensing device in accordance with claim 4 and further including means for preventing axial movement of said inner and outer members relative to each other, and means for limiting rotary movement of said inner and outer members relative to each other.

6. A dispenser in accordance with claim 1 and further including sealing means extending between said cylindrical portions of said inner and outer members.

7. A dispenser in accordance with claim 6 wherein said sealing means comprises an annular groove in one of said cylindrical portions, and an O-ring located in said groove and in sealing engagement with each of said inner and outer members.

8. A dispenser in accordance with claim 1 wherein said aperture means is in said outer member and comprises a restricted opening affording air flow therethrough.

9. A dispenser comprising an inner member including a portion having an axis and a first end closed by a transverse wall, being resiliently displaceable in the direction of said axis between a collapsed condition and a normally extended condition, and defining an interior cavity adapted to contain a substance in the form of a vapor, an outer member movable relative to said inner member with respect to said axis and including a generally cylindrical portion in closely fitting telescopic relation to said inner member and having a first open end adjacent said transverse wall of said inner member portion, and a second end, and a wall closing said second end of said outer member cylindrical portion, and aperture means for affording air flow therethrough relative to said interior cavity in response to displacement of said inner member portion between said collapsed and extended conditions, said aperture means including an open area located in each of said inner and outer members and movable relative to each other in response to relative movement between said inner and outer members between a first position wherein said open areas are in registration to afford air flow therethrough relative to said interior cavity and a second position wherein said open areas are spaced from each other to prevent air flow relative to said interior cavity.

10. A dispenser in accordance with claim 9 wherein said inner member portion is a bellows portion.

11. A dispenser in accordance with claim 9 wherein said inner member portion is a sponge-like portion.

12. A dispenser in accordance with claim 9 wherein said open areas are axially spaced when said inner and outer members are in said extended condition.

13. A dispenser in accordance with claim 9 wherein said open areas are annularly spaced when said inner and outer members are in said extended condition.

14. A dispenser in accordance with claim 9 wherein said inner member is of one-piece blow-molded construction.

15. A dispenser comprising an inner member including a portion having an axis and a first end closed by a transverse wall, being resiliently displaceable in the direction of said axis between a collapsed condition and a normally extended condition, and defining an interior cavity adapted to contain a substance in the form of a vapor, an outer member movable relative to said inner member with respect to said axis and including a generally cylindrical portion in closely fitting telescopic relation to said inner member and having a first open end adjacent said transverse wall of said inner member portion, and a second end, and a wall closing said second end of said outer member cylindrical portion, said inner and outer members being movable axially and rotatably relative to each other, means for causing rotary movement between said inner and outer members in response to axial movement, means for limiting axial movement between said inner and outer members, means for limiting rotary movement between said inner and outer members, and aperture means in at least one of said inner and outer members for affording air flow therethrough relative to said interior cavity in response to displacement of said inner member portion between said collapsed and extended conditions, whereby, the application of force in the direction of said axis causes axial movement of said outer member relative said inner member in the direction affording displacement of said inner member portion to the collapsed condition with accompanying discharge of air with the substance in vapor form from said interior cavity through said aperture means to the outer atmosphere, thereby dispensing the substance, and whereby release of the application of force causes axial movement of said outer member relative to said inner member in the direction affording re-extension of said inner member portion to the normally extended condition and inflow of air from the outer atmosphere into said interior cavity.

16. A dispenser comprising an inner member including a bellows portion having an axis and a first end closed by a transverse wall, being resiliently displaceable in the direction of said axis between a collapsed condition and a normally extended condition, and defining an interior cavity adapted to contain an envelope having a wall which is permeable to a substance contained therein and through which the substance passes into the immediately surrounding atmosphere as a vapor, an outer member movable relative to said inner member with respect to said axis, and including a generally cylindrical portion in closely fitting telescopic relation to said inner member and having a first open end adjacent said transverse wall of said bellows portion, and a second end, and a wall closing said second end of said outer member cylindrical portion, and means including an open area located in each of said inner and outer members and movable relative to each other in response to relative movement between said inner and outer members between a first position wherein said open areas are in registration to afford air flow therethrough relative to said interior cavity and a second position wherein said open areas are spaced from each other to prevent air flow relative to said interior cavity, whereby the application of force in the direction of said axis causes axial movement of said outer member relative said inner member in the direction affording displacement of said bellows portion to the collapsed condition with accompanying discharge of air with the substance in vapor form from said interior cavity through said open areas to the outer atmosphere, thereby dispensing the substance, and whereby release of the application of force causes axial movement of said outer member relative to said inner member in the direction affording re-extension of said bellows portion to the normally extended condition and inflow of air from the outer atmosphere into said interior cavity.

17. A dispenser comprising an inner member including a cylindrical portion having an axis and opposite first and second ends, a first transverse wall closing said first end of said cylindrical portion, and a bellows portion extending from said second end of said cylindrical portion, having an open end remote from said cylindrical portion, being resiliently displaceable in the direction of said axis between a collapsed condition and a normally extended condition, and defining an interior cavity adapted to contain an envelope having a wall which is permeable to a substance contained therein and through which the substance passes into the immediately surrounding atmosphere as a vapor, an outer member movable relative to said inner member with respect to said axis and including a generally cylindrical portion in closely fitting telescopic relation to said cylindrical portion of said inner member and having a first open end extending beyond said bellows portion and to said cylindrical portion of said inner member, and a second end, and a transverse wall closing said second end of said cylindrical portion of said outer member, and an aperture located in each of said inner and outer members and movable relative to each other in response to relative movement between said inner and outer members between a first position wherein said apertures are in registration to afford air flow therethrough relative to said interior cavity and a second position wherein said aperture are spaced from each other to prevent air flow relative to said interior cavity, whereby, the application of force in the direction of said axis causes axial movement of said outer member relative said inner member in the direction affording displacement of said bellows portion to the collapsed condition with accompanying discharge of air with the substance in vapor form from said interior cavity through said apertures to the outer atmosphere, thereby dispensing the substance, and whereby release of the application of force causes axial movement of said outer member relative to said inner member in the direction affording re-extension of said bellows portion to the normally extended condition and inflow of air from the outer atmosphere into said interior cavity.

* * * * *